(12) United States Patent
Starns

(10) Patent No.: US 9,999,677 B1
(45) Date of Patent: Jun. 19, 2018

(54) WOUND HEALING COMPOSITION

(71) Applicant: Connie D. Starns, Harrisburg, IL (US)

(72) Inventor: Connie D. Starns, Harrisburg, IL (US)

( * ) Notice: Subject to any disclaimer, the term of this patent is extended or adjusted under 35 U.S.C. 154(b) by 604 days.

(21) Appl. No.: 14/641,362

(22) Filed: Mar. 7, 2015

(51) Int. Cl.

| | |
|---|---|
| *A61K 31/00* | (2006.01) |
| *A61K 36/15* | (2006.01) |
| *A61K 36/61* | (2006.01) |
| *A61K 47/46* | (2006.01) |
| *A61K 31/40* | (2006.01) |
| *A61K 31/655* | (2006.01) |
| *A61K 31/055* | (2006.01) |
| *A61K 47/14* | (2017.01) |
| *A61K 47/10* | (2017.01) |

(52) U.S. Cl.
CPC ............ *A61K 47/46* (2013.01); *A61K 31/055* (2013.01); *A61K 31/40* (2013.01); *A61K 31/655* (2013.01); *A61K 36/15* (2013.01); *A61K 36/61* (2013.01); *A61K 47/10* (2013.01); *A61K 47/14* (2013.01)

(58) Field of Classification Search
CPC ......... A61K 31/00; A61K 36/15; A61K 36/61
USPC ...................................... 424/278.1, 742, 770
See application file for complete search history.

(56) References Cited

U.S. PATENT DOCUMENTS

| | | | |
|---|---|---|---|
| 5,047,249 A | | 9/1991 | Rothman et al. |
| 5,973,010 A | * | 10/1999 | Crawford ............... A61K 35/04 424/43 |
| 6,399,091 B1 | * | 6/2002 | Berthold ............. A61M 31/002 424/443 |
| 7,785,584 B2 | * | 8/2010 | Jones ................... A61K 38/166 424/94.1 |
| 8,658,625 B2 | | 2/2014 | Inamoto et al. |

FOREIGN PATENT DOCUMENTS

CN    1481817 A  *  3/2004

OTHER PUBLICATIONS

Abdollah Ghasemi Pirbalouti, Shahrzad Azizf, Abed Koohpayeh and Behzad Hamedi, Wound Healing Activity of Malva Sylvestris and Punica Granatum in Alloxan-Induced Diabetic Rats, Acta Poloniac Pharmaceutica-Drug Research, vol. 67, No. 5, pp. 511-516, 2010.
Wonder Dust Advertisement, printed from the internet website: http://www.amazon.com/FARNAM-31101-Wonder-Oinment-4-Ounce/dp/B000QFQ90E/ref=sr_1_1?ie=UTF8&qid=1425494836 &sr=8-1&keywords=wonder+dust+wound+powder on Mar. 4, 2015.
Fura-Zone data sheet, printed from the internet website: http://www.neogen.com/AnimalSafety/pdf/ProdInfo/Tech_Bulletins/Fura-Zone.pdf on Mar. 4, 2015.
Scarlet Oil advertisement, printed from the internet website: http://www.vedco.com/index.php/product-listing/181-VINV-OLIS-SCAR on Mar. 4, 2015.

* cited by examiner

*Primary Examiner* — Christopher R Tate
*Assistant Examiner* — Deborah A Davis
(74) *Attorney, Agent, or Firm* — Grace J. Fishel

(57) ABSTRACT

A wound healing composition and method for wound healing utilizing a nitrofurazone in a water soluble ointment, activated charcoal, caustic and biebrich scarlet. Applying the composition to the wound and observing epithelial healing along the sides and bottom of the wound. Stopping treatment when the epithelial tissue fills the wound.

7 Claims, 1 Drawing Sheet

WOUND HEALING COMPOSITION

BACKGROUND OF THE INVENTION

1. Field of the Invention

The present invention relates to a composition and method for wound healing.

2. Brief Description of the Prior Art

Wounds that involve some degree of tissue loss with edges that cannot be easily approximated heal by secondary intention. Secondary intention is a dynamic process which can be divided into three phases: inflammation, proliferation and wound contraction.

Following injury, red blood cells form a blood clot, which creates a temporary barrier to pathogens from getting into the open wound. During the inflammation phase, the body sends white blood cells to capture and fight off any rogue bacteria that happen to get through the clot. The central event during the proliferation phase is the formation of granulation tissue followed by epitheliazation. Granulation tissue includes inflammatory cells and fibroblasts in a matrix of collagen. Exuberant growth of granulation tissue, e.g., proud flesh, may get in way of epitheliazation which occurs, primarily from the wound edges. In the final phase, the wound is contracted by myofibroblasts, which grip the wound edges and undergo contraction using a mechanism similar to that in smooth muscle cells.

It is critical to remember that wound healing is not a linear process and wounds can progress both forwards and back through the phases depending upon intrinsic and extrinsic forces at work within the patient. While one medication may be useful during the inflammatory phase, it may inhibit the formulation of granulation tissue or epitheliazation during the proliferation phase. During the proliferation phase, the removal of excess granulation tissue may require other medications which are contra-indicated for the inflammatory phase. Still yet other medications may stimulate epitheliazation but interfere with the other phases.

In view of the above, what is needed and not provided by the prior art is a wound healing composition that provides a balanced treatment during all three phases of secondary intention and can be applied throughout the healing process.

BRIEF SUMMARY OF THE INVENTION

In view of the above, it is an object of the present invention to provide an improved composition and method for treating epidermal wounds which do not respond to conventional pharmaceutical compositions and treatment methods. Other objects and features of the invention will be in part apparent and in part pointed out hereinafter.

In accordance with the invention, a wound healing composition comprising nitrofurazone in a water soluble ointment, activated charcoal, caustic and biebrich scarlet. In one embodiment, the charcoal and caustic are provided as a power wherein the charcoal comprising about one part to 14 parts hydrated lime. In other embodiments, the nitrofurazone ointment comprises about 0.2% by weight nitrofurazone in polyethylene glycols. In yet other embodiments, the biebrich scarlet is formulated in mineral oil and further includes parachlorometaxylenol. The wound healing composition is prepared by admixing all of the ingredients above noted. It is then applied to a clean open wound, possibly multiple times on day one. In the following days, the applications may become less frequent as the wound heals from the sides and bottom up. The compositions and methods are useful for treating wounds, diabetic ulcers, bed sores and the like of civilian patients and for use by military personnel in field operations.

The invention summarized above comprises the compositions and methods hereinafter described, the scope of the invention being indicated by the subjoined claims.

BRIEF DESCRIPTION OF THE SEVERAL VIEWS OF THE DRAWING

In the accompanying drawings, in which one of various possible embodiments of the invention are illustrated, corresponding reference characters refer to corresponding parts throughout the several views of the drawings in which.

DETAILED DESCRIPTION OF THE INVENTION

Figure 1:
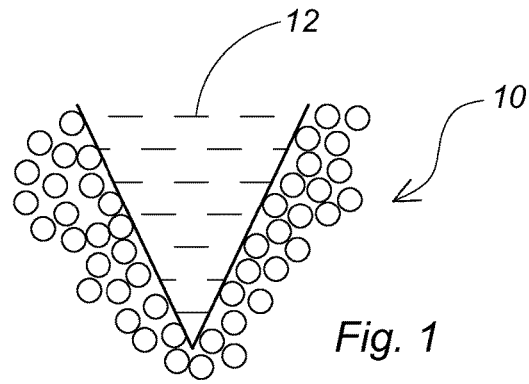
FIG. 1 is a schematic view of a wound into which a composition in accordance with the present invention has been applied on day one.

Before the compositions and methods of the present invention are described, it is to be understood that the invention is not limited to the particular methodologies, protocols and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice of the present invention, the preferred compositions and methods are now described.

The composition of the present invention includes nitrofurazone in a water soluble ointment, activated charcoal, caustic and biebrich scarlet. Without being limited by any theory, it is believed that the administration of a therapeutically effective amount of one or more of the compositions described herein to a wound with edges that cannot be approximated will promote the healing of the wound by simultaneously facilitating all three phases of secondary intention.

The nitrofurazone may be provided in a water soluble ointment which promotes absorption. Suitable examples include 0.2% by weight nitrofurazone in a water soluble base of polyethylene glycols which is commercially sold as FURA-ZONE solution by Neogen Corporation, 944 Nandino Blvd., Lexington, Ky. 40511. Nitrofurazone is an anti-infective agent with a broad antibacterial spectrum which is helpful in the inflammatory phase of wound healing.

Activated charcoal has internal spaces or pores in which chemicals may be trapped. As such, activated charcoal is highly absorbent and may be used as drying agent. In powdered form activated charcoal may be mixed with a caustic such as hydrated lime for use in removing excess granulation tissue in a ratio of about 1 part charcoal to 14 parts caustic. While the caustic eats away exuberant granulation tissue, it may also destroy healthy cells and as such must be used in moderation. A commercially available activated charcoal is sold as WONDER DUST by Farnam Companies, Inc., 301 West Osborn Road #2000, Phoenix, Ariz. 85013. WONDER DUST contains 5% by weight activated charcoal and 71.0% by weight hydrated lime. Addition ingredients include 2% by weight iodoform (an antiseptic), 5% by weight potassium alum (an antimicrobial), 2% by weight flowers of sulfur (an antiseptic), 2% by weight tannic acid (an astringent) and 13% by weight copper sulfate (a fungicide). In addition to being a caustic and raising the pH, hydrated lime is physiologically active and affects the permeability of cell membranes.

Biebrich scarlet is an epithelial stimulant and is commonly provided in mineral oil. One representative commercially available product is sold by Vedco, Inc., 5503 Corporate Drive, St Joseph, Mo. 64507 as SCARLET OIL and additionally contains parachlorometaxylenol (an antiseptic), methyl salicylate (a counterirritant), oil of eucalyptus (an anti-inflammatory), benzyl alcohol and isopropyl alcohol (solvents) and pine oil (an anti-inflammatory).

A composition according to the present invention is formed by blending the activated charcoal, caustic, biebrich scarlet into the nitrofurazone ointment. When the activated charcoal and caustic are provided as WONDER DUST and the biebrich scarlet is provided as SCARLET OIL, one embodiment of the invention may be formed by kneading ½ cup of WONDER DUST into 1 pound of FURA-ZONE. During this process, the operator should wear a dust mask. Three tablespoons of SCARLET OIL are then worked into the blend and the mixture put into the FURA-ZONE salve container.

A composition in accordance with the present invention such as the embodiment described above, may be used to treat wounds, the edges of which may not be approximated and joined with stitches, staples, flaps or the like. In use, the wound is cleaned with 0.9% by weight NaCL solution, patted dry and the composition applied directly into the wound with a spatula, finger or other tool. If the wound is dirty, it may be necessary to clean the wound first with soap and water before applying the wound healing composition. Application of a bandage is optional.

Figure 2:
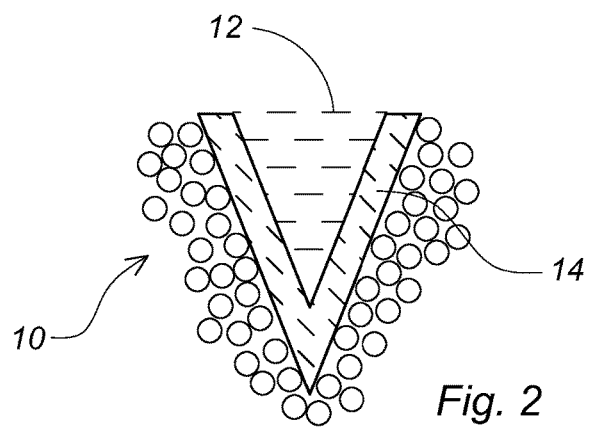
FIG. 2 is a later view of the wound showing epitheliazation in process along the sides and bottom of the wound.
Figure 3:
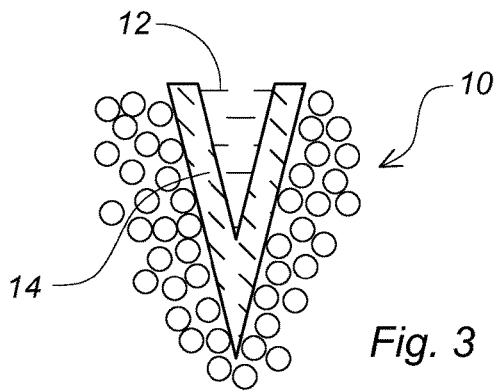
FIG. 3 is a still later view showing the healing progression from the sides and bottom up; and, FIG. 4 is a view of the healed wound capped with a scab.
Figure 4:
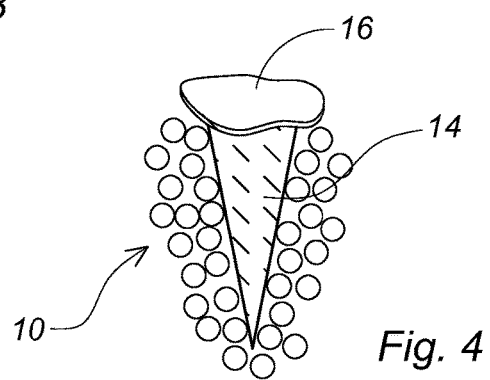

Initially it may be necessary to treat a wound 10 several times a day. This is done by first washing the wound to remove any loose tissue. The wound 10 is then packed with the healing composition 12 as shown in FIG. 1. As healing progresses, it may be possible to leave the wound healing composition in place for a longer periods of time. As shown in FIGS. 2-4, epitheliazation 14 starts along the side edges of the wound and is from bottom up. In due course, the wound 10 will close and a scab form 16 while new blood vessels penetrate the wound site and complete the healing process.

The following examples are given by way of illustration and do not limit the scope the invention. The example illustrates surprising results which have been obtained by utilizing the composition of the invention which other conventional wound treatments have been attempted and have failed in connection with treating the wounds.

Example 1

A would healing composition was prepared by blending together 1 pound of FURA-ZONE with ½ cup WONDER DUST. The operator wore a dust mask while kneading the WONDER DUST into the FURA-ZONE. Three tablespoons of SCARLET OIL were then worked into the kneaded mixture until a uniform paste was obtained.

Example 2

A white male about 55 years old with diabetes and a deep foot ulcer which had been resistant to treatment and with whom the need for possible amputation had been discussed, was treated as follows: On the first day, the wound was cleaned with soap and water and packed with the wound healing composition of Example 1. Initially the patient reported no sensation but in about 8-9 minutes reported that his foot felt a strong pressure lasting about five minutes during the cauterization phase. Thereafter, he reported he felt no other sensations. On day two and for four days, the wound was washed out with soap and water and the wound healing composition applied. On the fourth day, the tissue had come to the surface of the wound and a scab had attached to the top. Pink tissue had formed about 1 to 1½ inches around the wound. The composition was applied to the edges of the wound for three more days. On the seventh day, a scab had formed that was attached to the sides of the wound and treatment was discontinued. Circulation was restored in the wound and pink tissue surrounded the wound. A practicing podiatrist based on his 27 years of practice who saw the wound before and after treatment reported that he was aware of no deleterious effects and that the demonstrated healing capacity of the wound composition was remarkable.

From the foregoing description, various modifications and changes in the compositions and methods will occur to those skilled in the art. All such modifications coming within the scope of the appended claims are intended to be included therein.

What is claimed:

1. A wound healing composition comprising a nitrofurazone in a water soluble ointment, an activated charcoal, a caustic agent, and biebrich scarlet, wherein said composition is formed by the steps of:
    blending 1 pound of an ointment that contains 0.2% by weight of nitrofurazone and a water soluble base of polyethylene glycol, with a half a cup of a powdered activated charcoal that contains an effective amount of a caustic agent to form a mixture;
    kneading three tablespoons of mineral oil that contains an effective amount of biebrich scarlet into the mixture to obtain said wound healing composition.

2. The composition of claim 1 wherein the mineral oil further contains parachlorometaxylenol and the caustic is hydrated lime.

3. The wound healing composition of claim 2 wherein said powdered activated charcoal further includes iodoform, potassium alum, sublimed sulfur, tannic acid and copper sulfate.

4. The wound healing composition of claim 1 wherein said mineral oil further includes parachlorometaxylenol, methyl salicylate, oil of eucalyptus, benzyl alcohol, isopropyl alcohol and pine oil.

5. The wound healing composition of claim 4 wherein the benzyl alcohol comprises about 2.4% V/V of the mineral oil and the isopropyl alcohol comprises about 32.1 v/V of the mineral oil.

6. A method for treating a wound with side edges that cannot be approximated, said method comprising the steps of:
    cleaning the wound; and applying the wound healing composition of claim 1 to the wound in an amount effective to fill the wound.

7. The method of claim 6 further comprising observing epithelial healing along the sides and bottom of the wound after application of the wound healing composition and stopping treatment when the epithelial tissue fills the wound.

\* \* \* \* \*